United States Patent
Nakano

(10) Patent No.: US 6,229,050 B1
(45) Date of Patent: May 8, 2001

(54) PROCESS FOR THE PREPARATION OF HYDROXYADAMANTANONE DERIVATIVES

(75) Inventor: Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/647,460

(22) PCT Filed: Jan. 25, 2000

(86) PCT No.: PCT/JP00/00346

§ 371 Date: Sep. 29, 2000

§ 102(e) Date: Sep. 29, 2000

(87) PCT Pub. No.: WO00/44702

PCT Pub. Date: Aug. 3, 2000

(30) Foreign Application Priority Data

Jan. 29, 1999 (JP) ................................. 11-021735

(51) Int. Cl.$^7$ .................................................. C07C 45/61
(52) U.S. Cl. ........................................... 568/344; 568/351
(58) Field of Search ..................... 568/344, 351

(56) References Cited

U.S. PATENT DOCUMENTS 5,430,193 * 7/1995 Shen.
5,981,420 * 11/1999 Nakano et al.

FOREIGN PATENT DOCUMENTS 0858835   8/1998   (EP).

OTHER PUBLICATIONS

Srivastava, S. and Le Noble, W. "5–Hydroxy-adamantan–2–One", Synthetic Commun., 1984, vol. 14, No. 2, pp. 65–68.

Stetter, Hermann and Lennartz Jozef, "Cyclizations On The Basis of Bicyclo [3.3.1) nonane–3,7,9–trione", Justus Liebigs Ann. Chem., 1977, No. 11–1, pp. 1807–1826.

* cited by examiner

*Primary Examiner*—Johann Richter
*Assistant Examiner*—Sikarl A. Witherspoon

(57) ABSTRACT

The invented process produces a corresponding 5-hydroxy-2-adamantanone derivative by allowing a 2-adamantanone derivative of the following formula (1):

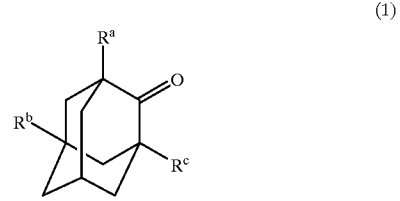

(1)

wherein each of $R^a$, $R^b$, and $R^c$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, or a nitro group, and of carbon atoms constituting an adamantane skeleton, the other carbon atoms than carbon atoms at bridgehead positions and at a bonding position of an oxo group may have a substituent, to react with oxygen in the presence of N-hydroxyphthalimide or another imide compound, a vanadium compound, and a manganese compound.

4 Claims, No Drawings

PROCESS FOR THE PREPARATION OF HYDROXYADAMANTANONE DERIVATIVES

This application is the national phase under 35 U.S.C. §371 of PCT International Application No. PCT/JP00/00346 which has an International filing date of Jan. 25, 2000, which designated the United States of America.

TECHNICAL FIELD

The present invention relates to a process for producing a hydroxyadamantanone derivative which is useful as a monomer or a material thereof for use in photosensitive resins and other functional polymers.

BACKGROUND ART

Alicyclic compounds each having a ring combined with a hydroxyl group are used, for example, as monomers or materials thereof for use in photosensitive resins and other functional polymers, and as intermediates of pharmaceuticals. Likewise, 5-hydroxy-2-adamantanone having an adamantane ring combined with a hydroxyl group is expected to be used as a monomer or a material thereof for use in resist resins, taking advantage of its unique cyclic structure.

Japanese Unexamined Patent Application Publication No. 9-327626 discloses a process for oxidizing adamantane with molecular oxygen by catalysis of a specific imide compound or of the imide compound and a metallic compound (refer to examples). However, the yield of 5-hydroxy-2-adamantanone having a hydroxyl group and an oxo group on an adamantane ring is very low according to this process, although adamantanol and adamantanepolyols can be obtained in good yields.

DISCLOSURE OF INVENTION

Accordingly, an object of the present invention is to provide a process for obtaining 5-hydroxy-2-adamantanone in a good yield.

After intensive investigations to achieve the above object, the present inventors found that a corresponding 5-hydroxy-2-adamantanone derivative can be produced in a good yield by oxidizing a 2-adamantanone derivative with oxygen in the presence of a catalyst including a combination of an imide compound having a specific structure and specific two metallic compounds. The present invention has been accomplished based on these findings.

Specifically, the present invention provides a process for producing a hydroxyadamantanone derivative. This process includes the step of allowing a 2-adamantanone derivative represented by the following formula (1):

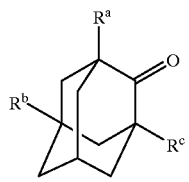

(1)

wherein each of $R^a$, $R^b$, and $R^c$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, or a nitro group, and of carbon atoms constituting an adamantane skeleton, the other carbon atoms than carbon atoms at bridgehead positions and at a bonding position of an oxo group may have a substituent, to react with oxygen in the presence of an imide compound represented by the following formula (2):

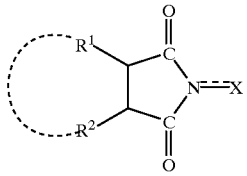

(2)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group; and one or two of N-substituted cyclic imido group indicated in the formula (2) may be further formed on the $R^1$, $R^2$, or on the double bond or aromatic or non-aromatic ring formed together by $R^1$ and $R^2$, a vanadium compound, and a manganese compound to yield a 5-hydroxy-2-adamantanone derivative represented by the following formula (3):

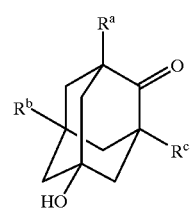

(3)

wherein $R^a$, $R^b$, and $R^c$ have the same meanings as defined above.

In this connection, the term "group protected by a protective group" used in the present description means a group which can be derived from a group to be protected (a free functional group) and contains the major component of the group to be protected. The compound represented by the formula (1) may be referred to as "substrate".

BEST MODE FOR CARRYING OUT THE INVENTION

2-Adamantanone Derivative

In the formula (1), the halogen atom in $R^a$, $R^b$, and $R^c$ includes, for example, fluorine, chlorine, and bromine atoms. The alkyl group includes, but is not limited to, methyl, ethyl, propyl, isopropyl, butyl, isobutyl, s-butyl, t-butyl, pentyl, hexyl, octyl, and decyl groups, and other alkyl groups having about 1 to 10 carbon atoms, preferably about 1 to 6 carbon atoms, and more preferably about 1 to 4 carbon atoms. Typically preferred alkyl groups are methyl group and ethyl group, of which methyl group is especially preferred.

The protective groups for hydroxyl group and hydroxymethyl group include conventional protective groups. Such protective groups include, but are not limited to, alkyl groups (e.g., methyl, and t-butyl groups, and other $C_1$–$C_4$ alkyl groups), alkenyl groups (e.g., allyl group), cycloalkyl groups (e.g., cyclohexyl group), aryl groups (e.g., 2,4- dinitrophenyl group), aralkyl groups (e.g., benzyl, 2,6-dichlorobenzyl, 3-bromobenzyl, 2-nitrobenzyl, and triphenylmethyl groups), substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, and 2,2,2-trichloroethyl groups), tetrahydropyranyl group, tetrahydrofuranyl group, acyl groups (e.g., formyl, acetyl, propionyl, butyryl, isobutyryl, valeryl, and pivaloyl groups, and other $C_1$–$C_6$ aliphatic acyl groups; acetoacetyl group; benzoyl, and naphthoyl groups, and other aromatic acyl groups), alkoxycarbonyl groups (e.g., methoxycarbonyl, ethoxycarbonyl, and t-butoxycarbonyl groups, and other $C_1$–$C_4$-alkoxy-carbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups). When the molecule to be protected has two or more hydroxyl groups (inclusive of hydroxymethyl groups), the protective groups also include divalent hydrocarbon groups (e.g., methylene, ethylidene, isopropylidene, cyclopentylidene, cyclohexylidene, and benzylidene groups) which may have a substituent. Preferred protective groups for hydroxyl group or the like include, for example, $C_1$–$C_4$ alkyl groups, substituted methyl groups, substituted ethyl groups, acyl groups, $C_1$–$C_4$ alkoxy-carbonyl groups, substituted or unsubstituted carbamoyl groups, and divalent hydrocarbon groups which may have a substituent.

Protective groups for amino group include the aforementioned alkyl groups, aralkyl groups, acyl groups, alkoxycarbonyl groups, aralkyloxycarbonyl groups, dialkylphosphinothioyl groups, and diarylphoshinothioyl groups mentioned as the protective groups for hydroxyl group. Preferred protective groups for amino group are, for example, $C_1$–$C_4$ alkyl groups, $C_2$–$C_6$ aliphatic acyl groups, aromatic acyl groups, and $C_1$–$C_4$ alkoxy-carbonyl groups.

Illustrative protective groups for carboxyl group include, but are not limited to, alkoxy groups (e.g., methoxy, ethoxy, butoxy, and other $C_1$–$C_6$ alkoxy groups), cycloalkyloxy groups, aryloxy groups (e.g., phenoxy group), aralkyloxy groups (e.g., benzyloxy group), trialkylsilyloxy groups (e.g., trimethylsilyloxy group), amino groups which may have a substituent (e.g., amino group; methylamino group, dimethylamino group, and other mono- or di-$C_1$–$C_6$ alkylamino groups), hydrazino group, alkoxycarbonylhydrazino groups, and aralkyloxycarbonylhydrazino groups. Preferred examples of the protective groups for carboxyl group are $C_1$–$C_6$ alkoxy groups (especially, $C_1$–$C_4$ alkoxy groups), and mono- or di-$C_1$–$C_6$ alkylamino groups (especially, mono- or di-$C_1$–$C_4$ alkylamino groups).

Of carbon atoms constituting an adamantane skeleton, the other carbon atoms than carbon atoms at bridgehead positions and at a bonding position of an oxo group indicated in the formula (1) may have a substituent. Such substituents include, but are not limited to, oxo group, alkyl groups (e.g., methyl group, and other $C_1$–$C_4$ alkyl groups), acyl groups (e.g., acetyl group, and other $C_2$–$C_5$ aliphatic acyl groups, benzoyl group, and other arylcarbonyl groups), hydroxyl group which may be protected by such a protective group as mentioned above [e.g., hydroxyl group, alkoxy groups (e.g., methoxy group, and other $C_1$–$C_4$ alkoxy groups, substituted methyloxy groups, substituted ethyloxy groups), acyloxy groups (e.g., acetoxy, and other $C_2$–$C_6$ aliphatic acyloxy groups, acetoacetyloxy group, benzoyloxy group, and other arylcarbonyloxy groups)], carboxyl group which may be protected by such a protective group as mentioned above [e.g., carboxyl group, alkoxycarbonyl groups (e.g., methoxycarbonyl, ethoxycarbonyl, and other $C_1$–$C_4$ alkoxycarbonyl groups)], amino group which may be protected by such a protective group as mentioned above, halogen atoms (e.g., fluorine, chlorine, and bromine atoms), and cyano group. Typical 2-adamantanone derivatives include, for example, 2-adamantanone.

Imide Compound

An important feature of the present invention is the combination use of the imide compound represented by the formula (2), a vanadium compound, and a manganese compound as a catalyst. If the imide compound is used alone or if the imide compound and a manganese compound are used in combination, a reaction rate is low and a target compound 5-hydroxy-2-adamantanone derivative cannot be significantly obtained in a good yield. If a catalyst including the imide compound in combination with a vanadium compound is employed, side reactions such as a ring-opening reaction excessively occur, and the target compound cannot be significantly obtained in a good yield.

Of the substituents $R^1$ and $R^2$ in the formula (2), the halogen atom includes iodine, bromine, chlorine and fluorine. The alkyl group includes, but is not limited to, methyl, ethyl, propyl, isopropyl, butyl, isobutyl, s-butyl, t-butyl, pentyl, hexyl, heptyl, octyl, and decyl groups, and other straight- or branched-chain alkyl groups each having about 1 to 10 carbon atoms. Preferred alkyl groups are alkyl groups each having about 1 to 6 carbon atoms, of which lower alkyl groups each having about 1 to 4 carbon atoms are particularly preferred.

The aryl group includes phenyl and naphthyl groups, for example. Illustrative cycloalkyl groups include cyclopentyl, and cyclohexyl groups. Illustrative alkoxy groups are methoxy, ethoxy, propoxy, isopropoxy, butoxy, isobutoxy, t-butoxy, pentyloxy, and hexyloxy groups, and other alkoxy groups each having about 1 to 10 carbon atoms, and preferably having about 1 to 6 carbon atoms. Among them, lower alkoxy groups each having about 1 to 4 carbon atoms are especially preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. Preferred alkoxycarbonyl groups are alkoxycarbonyl groups each having about 1 to 6 carbon atoms in the alkoxy moiety, of which lower alkoxycarbonyl groups each having about 1 to 4 carbon atoms in the alkoxy moiety are particularly preferred.

Illustrative acyl groups include, for example, formyl, acetyl, propionyl, butyryl, isobutyryl, valeryl, isovaleryl, and pivaloyl groups, and other acyl groups each having about 1 to 6 carbon atoms.

The substituents $R^1$ and $R^2$ may be identical to or different from each other. The substituents $R^1$ and $R^2$ in the formula (2) may be combined to form a double bond, or an aromatic or non-aromatic ring. The preferred aromatic or non-aromatic ring has about 5 to 12 members, and particularly about 6 to 10 members. The ring may be a heterocyclic ring or condensed heterocyclic ring, but it is often a hydrocarbon ring. Such rings include, for example, non-aromatic alicyclic rings (e.g., cyclohexane ring, and other cycloalkane rings which may have a substituent, cyclohexene ring, and other cycloalkene rings which may have a substituent), non-aromatic bridged rings (e.g., 5-norbornene ring, and other bridged hydrocarbon rings which may have a substituent), benzene ring, naphthalene ring, and other aromatic rings (including condensed rings) which may have a substituent. The ring is composed of an aromatic ring in many cases. The ring may have a substituent. Such substituents include, but are not limited to, alkyl groups, haloalkyl groups, hydroxyl group, alkoxy groups, carboxyl group, alkoxycarbonyl groups, acyl groups, nitro group, cyano group, amino group, and halogen atoms.

In the formula (2), X represents an oxygen atom or a hydroxyl group, and the bond between the nitrogen atom N and X is a single bond or a double bond.

One or two of N-substituted cyclic imido group indicated in the formula (2) may be further formed on $R^1$, $R^2$, or on the double bond or aromatic or non-aromatic ring formed together by $R^1$ and $R^2$. For example, when $R^1$ or $R^2$ is an alkyl group having two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

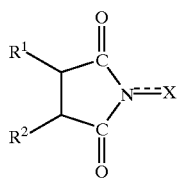

(2a)

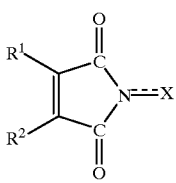

(2b)

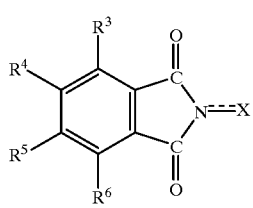

(2c)

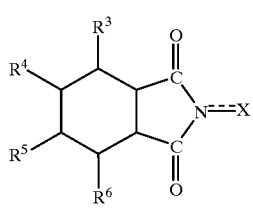

(2d)

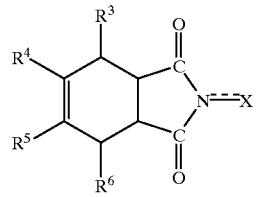

(2e)

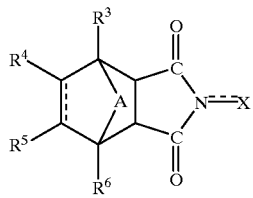

(2f)

wherein $R^3$ to $R^6$ are each, identical to or different from one another, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; in the formula (2f), A is a methylene group or an oxygen atom, and $R^1$, $R^2$ and X have the same meanings as defined above, where one or two of N-substituted cyclic imido group indicated in the formula (2c) may be further combined with the benzene ring in the formula (2c).

In the substituents $R^3$ to $R^6$, the alkyl group includes similar alkyl groups to those exemplified above, especially alkyl groups each having about 1 to 6 carbon atoms. The haloalkyl group includes trifluoromethyl group, and other haloalkyl groups each having about 1 to 4 carbon atoms. The alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. The acyl group includes similar acyl groups to those described above, especially acyl groups each having about 1 to 6 carbon atoms. The illustrative halogen atoms include fluorine, chlorine and bromine atoms. Each of the substituents $R^3$ to $R^6$ is often a hydrogen atom, a lower alkyl group having about 1 to 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5- to 12-membered rings are particularly preferred.

Typically preferred imide compounds include, for example, N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphtalenetetracarboximide.

The imide compounds represented by the formula (2) can be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

Such acid anhydrides include, but are not limited to, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds of the formula (2) can be used alone or in combination. The imide compounds can be used as being supported on a carrier. As such carriers, activated carbon, zeolite, silica, silica-alumina, bentonite, and other porous carries are frequently employed.

The proportion of the imide compound can be selected within a wide range and is, for example, about 0.0001 to 1 mole, preferably about 0.001 to 0.5 mole, more preferably about 0.01 to 0.4 mole, and often about 0.05 to 0.35 mole, relative to 1 mole of the substrate.

Vanadium Compound and Manganese Compound

As the vanadium compound and manganese compound, a wide variety of compounds each containing a vanadium atom or a manganese atom can be employed. Each of these vanadium compounds and manganese compounds can be respectively used alone or in combination. A vanadium element in the vanadium compound has a valency of 2 to 5, and a manganese element in the manganese compound has a valency of 1 to 7.

Such vanadium compounds and manganese compounds include, but are not limited to, hydroxides, oxides (including complex oxides), halides (fluorides, chlorides, bromides, and iodides), salts of oxoacids (e.g., nirates, sulfates, phosphates, borates, and carbonates), oxoacids, isopolyacids, heteropolyacids, and other inorganic compounds of each element; salts of organic acids (e.g., acetates, propionates, hydrocyanates, naphthenates, and stearates), complexes, and other organic compounds of each element. Ligands constituting the complexes include OH (hydroxo), alkoxy (e.g., methoxy, ethoxy, propoxy, and butoxy), acyl (e.g., acetylandpropionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (e.g., triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Typical vanadium compounds include, for example, vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valency of 2 to 5. Typical manganese compounds include, but are not limited to, manganese hydroxide, manganese oxide, manganese chloride, manganese bromide, manganese nitrate, manganese sulfate, manganese phosphate, and other inorganic compounds; manganese acetate, manganese naphthenate, manganese stearate, and other salts of organic acids; and acetylacetonatomanganese, and other complexes, and other divalent or trivalent manganese compounds.

The total amount of the vanadium compound and the manganese compound is, for example, about 0.0001 to 0.7 mole, preferably about 0.001 to 0.5 mole, more preferably about 0.0015 to 0.1 mole, and often about 0.0015 to 0.05 mole (particularly, about 0.002 to 0.01 mole), relative to 1 mole of the substrate.

The ratio (metallic atomic ratio) of the vanadium compound to the manganese compound is, for example, such that the former/the latter is about 99/1 to 1/99, preferably about 95/5 to 10/90, more preferably about 90/10 to 30/70, and often about 80/20 to 50/50.

The other metallic catalysts can be employed as promoters in combination with the above compounds within a range not deteriorating the rate and selectivity of the reaction.

Oxygen

As the oxygen, either of molecular oxygen and nascent oxygen can be used. Such molecular oxygen includes, but is not limited to, pure oxygen, and oxygen diluted with an inert gas such as nitrogen, helium, argon or carbon dioxide. Air is preferably used as the oxygen from the viewpoints of, for example, operating property and safety, as well as cost efficiency.

The amount of the oxygen can be appropriately selected depending on the type of the substrate and is generally equal to or more than about 0.5 mole (e.g., equal to or more than 1 mole), preferably about 1 to 100 moles, and more preferably about 2 to 50 moles, relative to 1 mole of the substrate. The oxygen is often used in excess moles relative to the substrate.

Reaction

The reaction is generally performed in an organic solvent. Such organic solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butylacetate, and other esters; and mixtures of these solvents. In may cases, acetic acid and other organic acids, acetonitrile, benzonitrile, and other nitrites, trifluoromethylbenzene, and other halogenated hydrocarbons, ethyl acetate and other esters are used as the solvent.

A reaction temperature can be appropriately selected depending on, for example, the types of reaction components and is, for example, about 0° C. to 300° C., preferably about 30° C. to 250° C., and more preferably about 40° C. to 200° C. The reaction is usually performed at a temperature of about 40° C. to 150° C. in many cases. The reaction can be performed at atmospheric pressure or under a pressure (under a load). When the reaction is conducted under a pressure, the pressure is usually about 1 to 100 atm (e.g. 1.5 to 80 atm), and preferably about 2 to 70 atm. A reaction time can be appropriately selected within a range of, for example, about 30 minutes to 48 hours depending on the reaction temperature and pressure. The reaction can be performed in a batch system, semi-batch system, continuous system or another conventional system in the presence of, or under flow of oxygen.

The invented process can selectively introduce a hydroxyl group at the 5-position upon reaction to yield a 5-hydroxy-2-adamantanone derivative in a good yield. After the completion of the reaction, reaction products can be easily separated and purified by a conventional technique such as filtration, concentration, distillation, extraction, crystallization, recrystallization, column chromatography, and other separation means, or any combination of these separation means.

According to the invented process, a 2-adamantanone derivative is oxidized with oxygen using a ternary catalyst including a combination of an imide compound having a specific structure, a vanadium compound, and a manganese compound, and a corresponding 5-hydroxy-2-adamantanone derivative can be obtained in a good yield.

The present invention will be illustrated in further detail with reference to several examples below, which are not intended to limit the scope of the invention.

EXAMPLE 1

A mixture of 0.1 mol of 2-adamantanone, 10 mmol of N-hydroxyphthalimide, 0.33 mmol of acetylacetonatovanadium $V(AA)_3$, 0.17 mmol of acetylacetonatomanganese $Mn(AA)_2$, and 250 ml of acetic acid was stirred at 80° C. in an oxygen atmosphere (1 atm) for 6 hours. The resulting reaction mixture was concentrated and was then extracted with ethyl acetate. A portion of an organic layer was concentrated and was then cooled for crystallization to yield 5-hydroxy-2-adamantanone (yield: 37%). The conversion rate from 2-adamantanone was 64%.

Spectrum Data of 5-Hydroxy-2-adamantanone

IR ($cm^{-1}$): 3410, 2920, 2810, 1720, 1440, 1330, 1240, 1060, 880 MS m/e: 166 ([$M^{+1}$, 148, 119.

EXAMPLE 2

A mixture of 0.1 mol of 2-adamantanone, 10 mmol of N-hydroxyphthalimide, 0.33 mmol of acetylacetonatovanadium $V(AA)_3$, 0.17 mmol of acetylacetonatomanganese $Mn(AA)_2$, and 250 ml of acetic acid was stirred at 85° C. in an oxygen atmosphere (1 atm) for 10 hours. The resulting reaction mixture was concentrated and was then extracted with ethyl acetate. A portion of an organic layer was concentrated and was then cooled for crystallization to yield 5-hydroxy-2-adamantanone (yield: 48%). The conversion rate from 2-adamantanone was 74%.

COMPARATIVE EXAMPLE 1

A mixture of 0.1 mol of 2-adamantanone, 10 mmol of N-hydroxyphthalimide, and 250 ml of acetic acid was stirred at 80° C. in an oxygen atmosphere (1 atm) for 6 hours. A gas chromatographic analysis of a reaction mixture found that the conversion rate from 2-adamantanone was 1% and the yield of 5-hydroxy-2-adamantanone was 0%.

COMPARATIVE EXAMPLE 2

A mixture of 0.1 mol of 2-adamantanone, 10 mmol of N-hydroxyphthalimide, 0.5 mmol of acetylacetonatovanadium $V(AA)_3$, and 250 ml of acetic acid was stirred at 80° C. in an oxygen atmosphere (1 atm) for 6 hours. A gas chromatographic analysis of a reaction mixture found that the conversion rate from 2-adamantanone was 65% and the yield of 5-hydroxy-2-adamantanone was 1%.

COMPARATIVE EXAMPLE 3

A mixture of 0.1 mol of 2-adamantanone, 10 mmol of N-hydroxyphthalimide, 0.5 mmol of acetylacetonatomanganese $Mn(AA)_2$, and 250 ml of acetic acid was stirred at 80° C. in an oxygen atmosphere (1 atm) for 6 hours. A gas chromatographic analysis of a reaction mixture found that the conversion rate from 2-adamantanone was 27% and the yield of 5-hydroxy-2-adamantanone was 4%.

I claim:

1. A process for producing a hydroxyadamantanone derivative, said process comprising the step of allowing a 2-adamantanone derivative represented by the following formula (1):

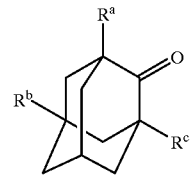

(1)

wherein each of $R^a$, $R^b$, and $R^c$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, or a nitro group, and of carbon atoms constituting an adamantane skeleton, the other carbon atoms than carbon atoms at bridgehead positions and at a bonding position of an oxo group may have a substituent, to react with oxygen in the presence of an imide compound represented by the following formula (2):

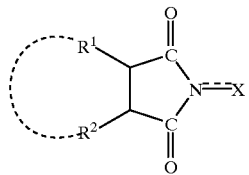

(2)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group; and one or two of N-substituted cyclic imido group indicated in the formula (2) may be further formed on said $R^1$, $R^2$, or on the double bond or aromatic or non-aromatic ring formed together by $R^1$ and $R^2$, a vanadium compound, and a manganese compound to yield a 5-hydroxy-2-adamantanone derivative represented by the following formula (3):

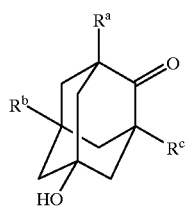

(3)

wherein $R^a$, $R^b$, and $R^c$ have the same meanings as defined above.

2. A process for producing a hydroxyadamantanone derivative according to claim 1, wherein $R^1$ and $R^2$ in the imide compound represented by the formula (2) are combined to form an aromatic or non-aromatic 5- to 12-membered ring.

3. A process for producing a hydroxyadamantanone derivative according to claim 1, wherein the total amount of said vanadium compound and said manganese compound is 0.0001 to 0.7 mole relative to 1 mole of the 2-adamantanone derivative represented by the formula (1).

4. A process for producing a hydroxyadamantanone derivative according to claim 1, wherein the ratio (metallic atomic ratio) of the vanadium compound to the manganese compound is such that the former/the latter is 99/1 to 1/99.

\* \* \* \* \*